United States Patent [19]
Wu et al.

[11] Patent Number: 5,702,392
[45] Date of Patent: Dec. 30, 1997

[54] COUPLING PLATE FOR SPINAL CORRECTION AND A CORRECTION DEVICE OF USING THE SAME

[76] Inventors: Shing-sheng Wu, 2nd Fl., No. 38-2, Sec. 3, Tingchou Rd.; Po-quang Chen, 1st Fl., No. 40-1, Lane 23, Yungkang St., both of Taipei, Taiwan

[21] Appl. No.: 533,101

[22] Filed: Sep. 25, 1995

[51] Int. Cl.$^6$ ............................................. A61B 17/70
[52] U.S. Cl. ........................ 606/61; 606/72; 606/73
[58] Field of Search ........................... 606/61, 60, 72, 606/73; 623/17

[56] References Cited

U.S. PATENT DOCUMENTS

| | | | |
|---|---|---|---|
| 4,815,453 | 3/1989 | Cotrel | 606/61 |
| 5,129,900 | 7/1992 | Asher et al. | 606/61 |
| 5,387,212 | 2/1995 | Yuan et al. | 606/61 |
| 5,437,669 | 8/1995 | Yuan et al. | 606/61 |
| 5,470,333 | 11/1995 | Ray | 606/61 |

Primary Examiner—Guy V. Tucker

[57] ABSTRACT

A coupling plate assembly for spinal correction includes a central rod, a clamping tube having a truncated conical head sized to receive the central rod, an integrally formed step, and a threaded inner periphery defining a hole on the step for a screw to extend therethrough and clamp the central rod, and a plate having two slots each extending from a distal end toward a center portion of the plate and a channel perpendicular to an interconnection axis of the slots with a groove for receiving the clamping tube.

4 Claims, 8 Drawing Sheets

COUPLING PLATE FOR SPINAL CORRECTION AND A CORRECTION DEVICE OF USING THE SAME

BACKGROUND OF THE INVENTION

The present invention relates to a correction device for spine, and particularly to a coupling plate assembly for the posterior spinal correction of a human being.

A conventional bone correction method for spine, which are in scoliosis or kyphosis, is either to apply Harrington Hooks on the laminae of the vertebrae or to execute a Luque Sublaminal Wiring thereby securing the vertebrae in place. However, such a correction method merely provides a correction of lateral direction, i.e., two dimensional correction. A C-D spinal instrumentation has a three dimensional correction, however, such a correction method is merely applied at one side of the spine, and thus strength applied on the spine is not balanced.

SUMMARY OF THE INVENTION

An object of the present invention is to provide a coupling plate which may easily cooperate with transpedicle screws and/or various hook assemblies to correct the deformed spine.

According to the present invention, the coupling plate assembly for spinal correction includes a central rod a clamping tube having a truncated conical head sized to receive the central rod, an integrally formed step, and a threaded inner periphery defining a hole on the step for a screw to extend therethrough and clamp the central rod, and a plate having two slots each extending from a distal end toward a center portion of the plate and a channel perpendicular to an interconnection axis of the slots with a groove for receiving the clamping tube.

Other objects, advantages, and novel features of the invention will become more apparent from the following detailed description when taken in conjunction with the accompanying drawings.

DETAILED DESCRIPTION OF THE PREFERRED EMBODIMENTS

Figure 1:
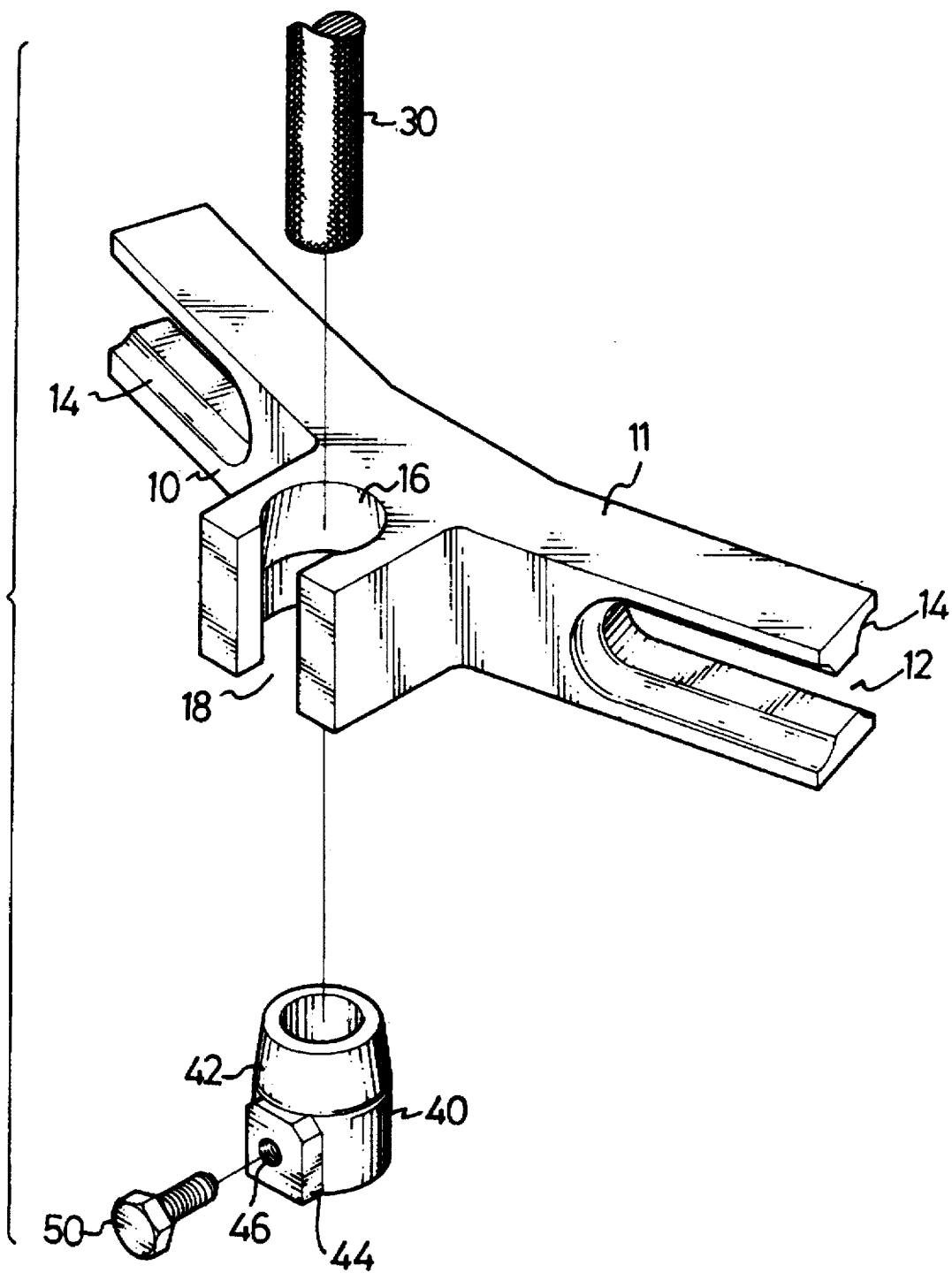
FIG. 1 is a perspective exploded view of a coupling plate assembly according to the present invention.

Referring to FIG. 1, a coupling plate assembly 10 for spinal correction includes an arcuate plate 11, two slots 12 each extending from a distal end toward a center portion of the plate 10 with grooved edges 14 on inner walls of the slots 12, a central rod 30, a clamping tube 40 with a truncated conical head 42 sized to receive the central rod 30 and an integrally formed step 44 having a threaded inner periphery defining a hole 46 which communicates with an inner wall space of the tube 40 for a screw 50 to extend therethrough and clamp the central rod 30, and a channel 16 perpendicular to an interconnected axis of the slots 12 with an opening 18 for receiving the clamping tube 40.

Figure 2:
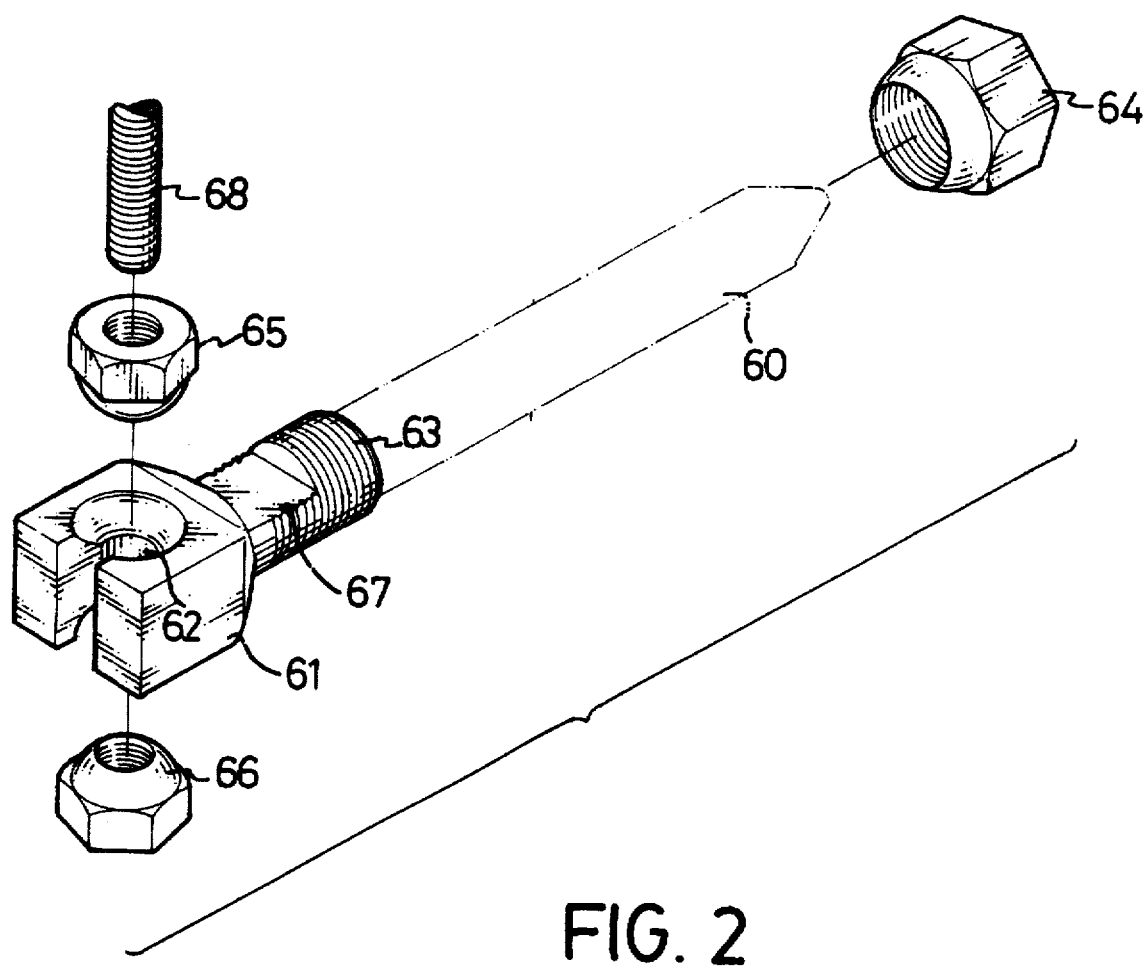
FIG. 2 is a perspective exploded view of a transpedicle screw assembly according to the present invention.

A transpedicle screw assembly cooperating with the coupling plate 10 of FIG. 1 is shown in FIG. 2. The transpedicle screw assembly includes a transpedicle screw 60 with a hole 62 defining in a head 61 of the screw 60 and two recesses 67 for engaging with the slot of the plate 10 and a threaded portion 63 formed near the head thereof, a cap nut 64 for engaging with the threaded portion 63 of the screw 60, two nuts 65, 66 respectively provided on entrances of the hole 62, and a threaded shaft 68 threaded with the nuts 65, 66 so that a position of the transpedicle screw 60 may be adjusted by turning the nuts 65, 66.

Figure 3:
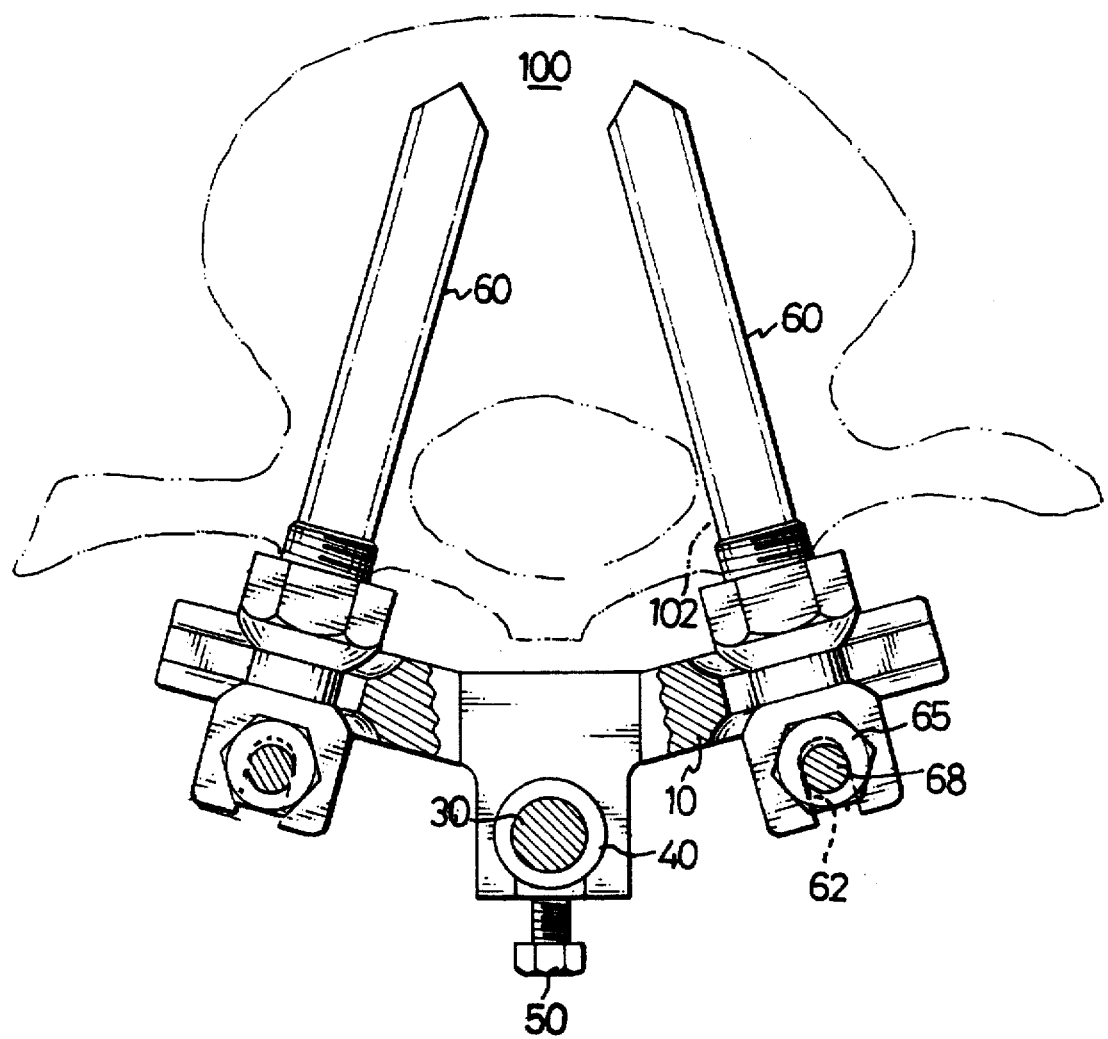
FIG. 3 is a schematic view of the coupling plate assembly according to the present invention in combination with the transpedicle screw assemblies of FIG. 2.

Referring to FIG. 3, two transpedicle screws 60 are driven into the vertebral body 100 via respective pedicle 102 and coupled with a coupling plate 10, the central rod 30 is received within the clamping tube 40 and clamped by the screw 50, and the threaded shafts 68 have respectively extended through the nut 65, the hole 62 on the transpedicle screw 60, and the nut 66 (not shown).

Figure 4:
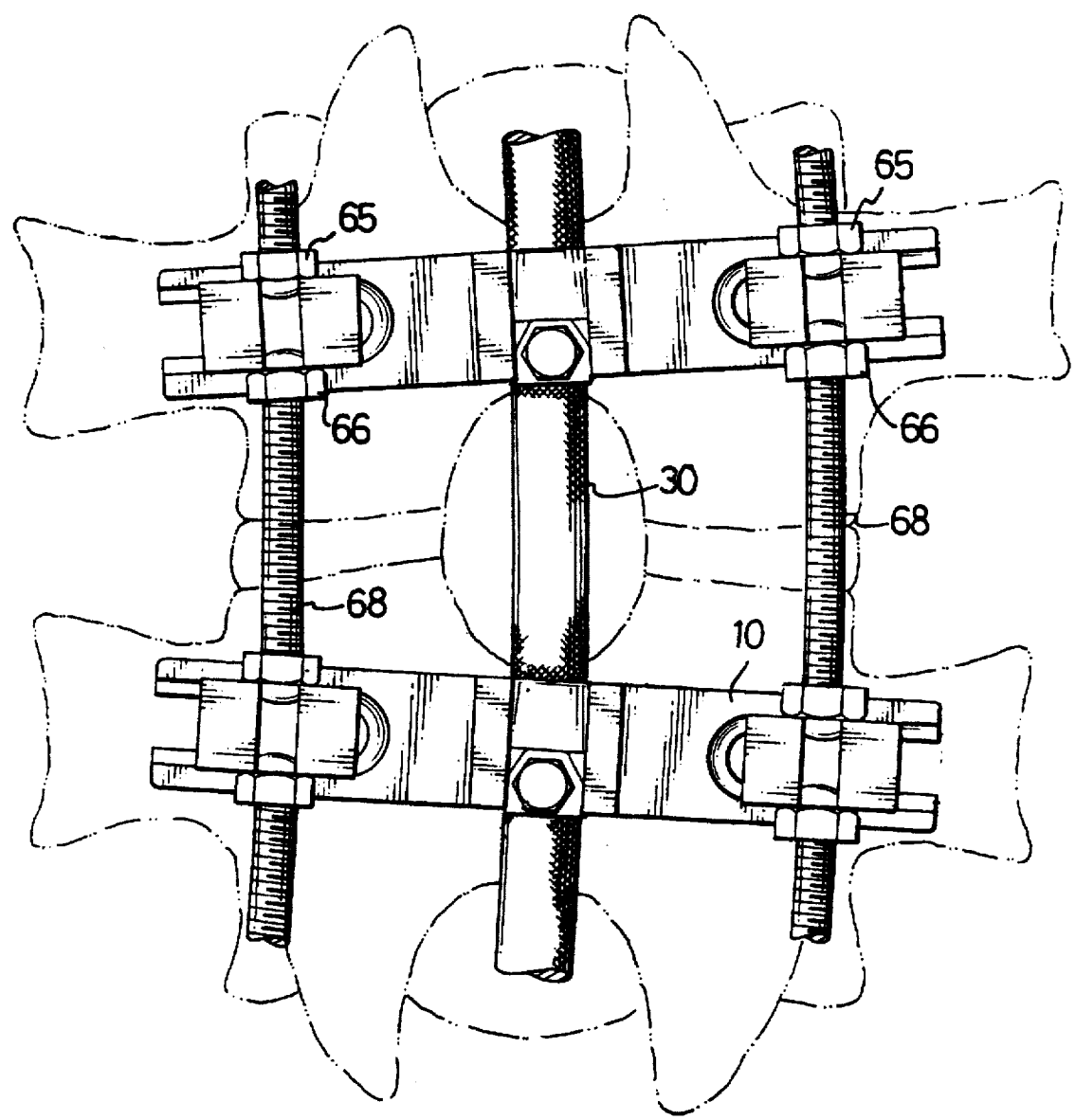
FIG. 4 is a schematic view of vertebrae in combination with a plurality of coupling plate assemblies according to the present invention and the transpedicle screw assemblies of FIG. 3.

Referring to FIG. 4, two coupling plate assemblies are respectively mounted onto two vertebrae with one central rod 30 and two threaded shafts 68 connected therebetween so that a three-dimensional correction may be achieved by adjusting the nuts 65, 66 and the central rod 30.

However, such a transpedicle screw 60 can only be applied onto a lumbar spine but is not suitable for a vertebra, which has a small volume, such as a thoracic spine, as the transpedicle screw may possibly damage a pedicle of the vertebrae.

Figure 5:
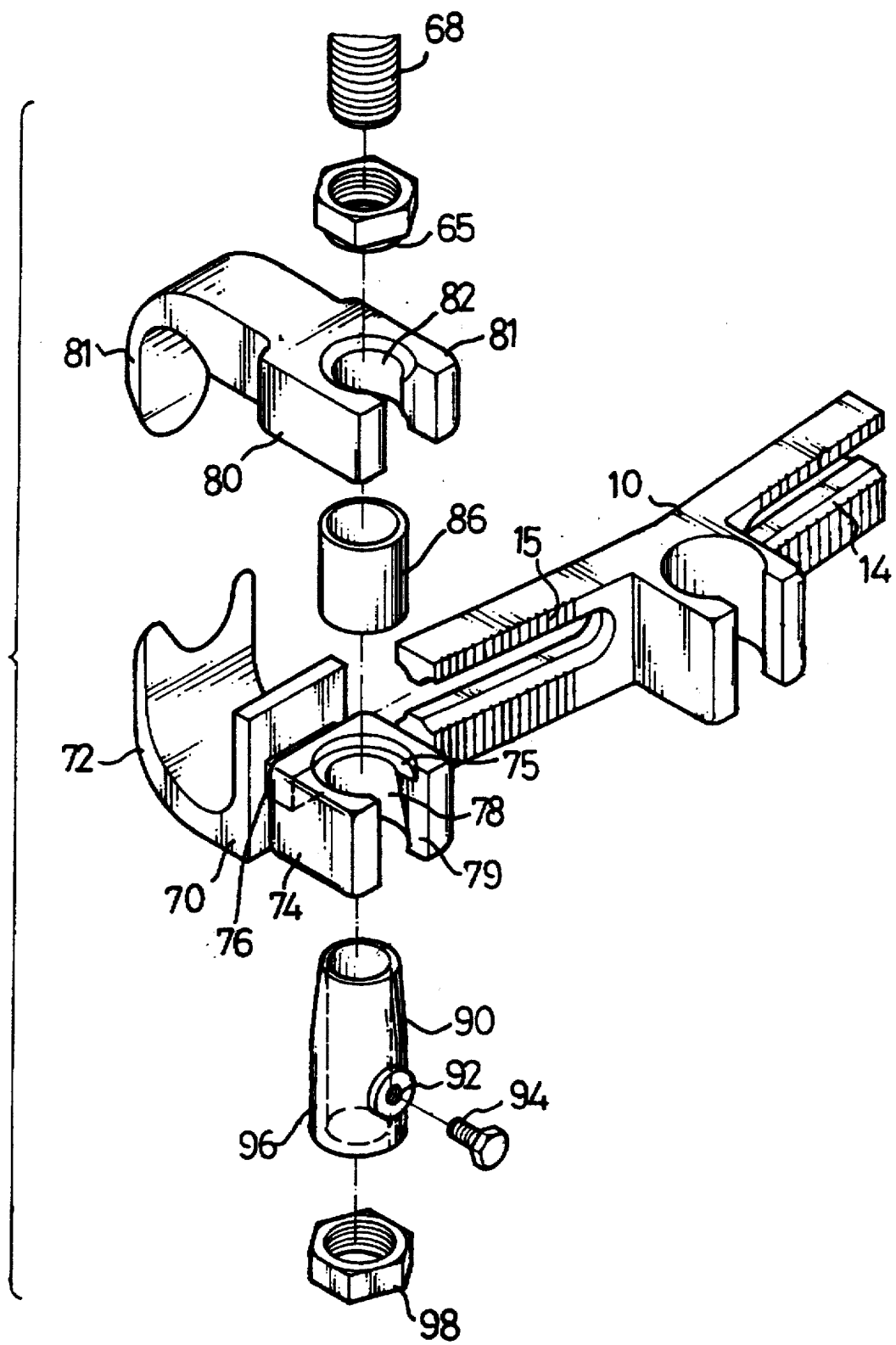
FIG. 5 is a perspective exploded view of a hook assembly in cooperation with a coupling plate according to the present invention.

Referring to FIG. 5, a hook assembly and a coupling plate 10 for applying onto a thoracic spine is shown. The hook assembly includes a threaded shaft 68, a nut 65, a transverse process hook 80, a tubular piece 86, a pedicle hook 70, a socket 90, and a nut 98 sequentially engaged with the threaded shaft 68. The coupling plate 10 has a plurality of notches 15 formed on surfaces defining the grooved edges 14.

The socket 90 is of a conical shape having a threaded inner periphery defining a hole 92 in combination with a screw 94 for clamping the threaded shaft 68 within the socket 90 when the hook assembly is assembled. A notched area 96 is formed on a location radially-opposite to the hole 92 for engaging with the notches 15 on the coupling plate 10 thereby increasing the stability of the hook assembly when assembled.

The pedicle hook 70 includes a U-shaped hook 72 defining a concave surface sized to cradle an inferior particular process (not shown) and a coupling body 74 attached to a wall of the hook 72 via an engaging piece 76 having a dimension to be received within the slot 12 of the coupling plate 10.

The coupling body 74 has a conical chamber 78 perpendicular to an axis of the concave surface of the U-shaped hook 72 for marginally receiving the socket 90, a groove 79 defined on a wall of the body 74 in communication with the conical chamber 78, and a depression 75 defined on a top surface of the coupling body 74 in communication with the conical chamber 78 for engaging with the tubular piece 86.

Figure 6:
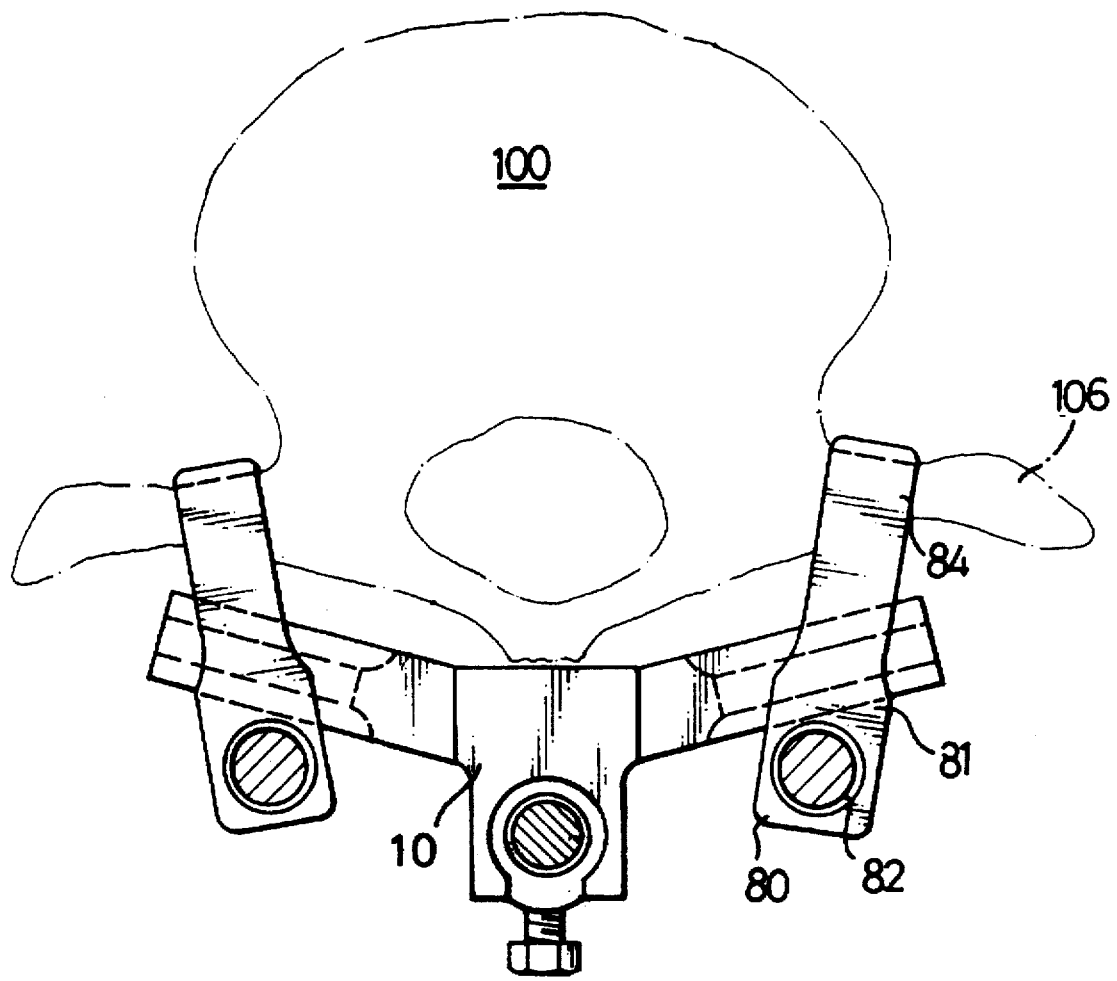
FIG. 6 is a schematic view of the coupling plate according to the present invention in combination with the transverse process hook assemblies of FIG. 2.

The transverse process hook 80 includes a block 81 having an aperture 82, a tongue 84 protruding from the body 81 for forming a concave surface facing the U-shaped hook 72 (in FIG. 5) to cradle a transverse process 106 of a vertebral body 100 as shown in FIG. 6. Referring back to FIG. 5, the aperture 82 has an enlarged depression edge (not shown) at a bottom of the block 81 for engaging with the tubular piece 86.

The nut 98 is provided under the socket 90 for engaging with the threaded shaft 68. The nut 65 cooperates with the nut 98 for tightly securing the socket 90, the pedicle hook 70, the tubular piece 86, and the transverse process hook 80 on the threaded shaft 68. The size of the tubular piece 86 may be changed corresponding to the size of the vertebra 70 until a suitable size of tubular piece 86 is achieved.

Figure 7:
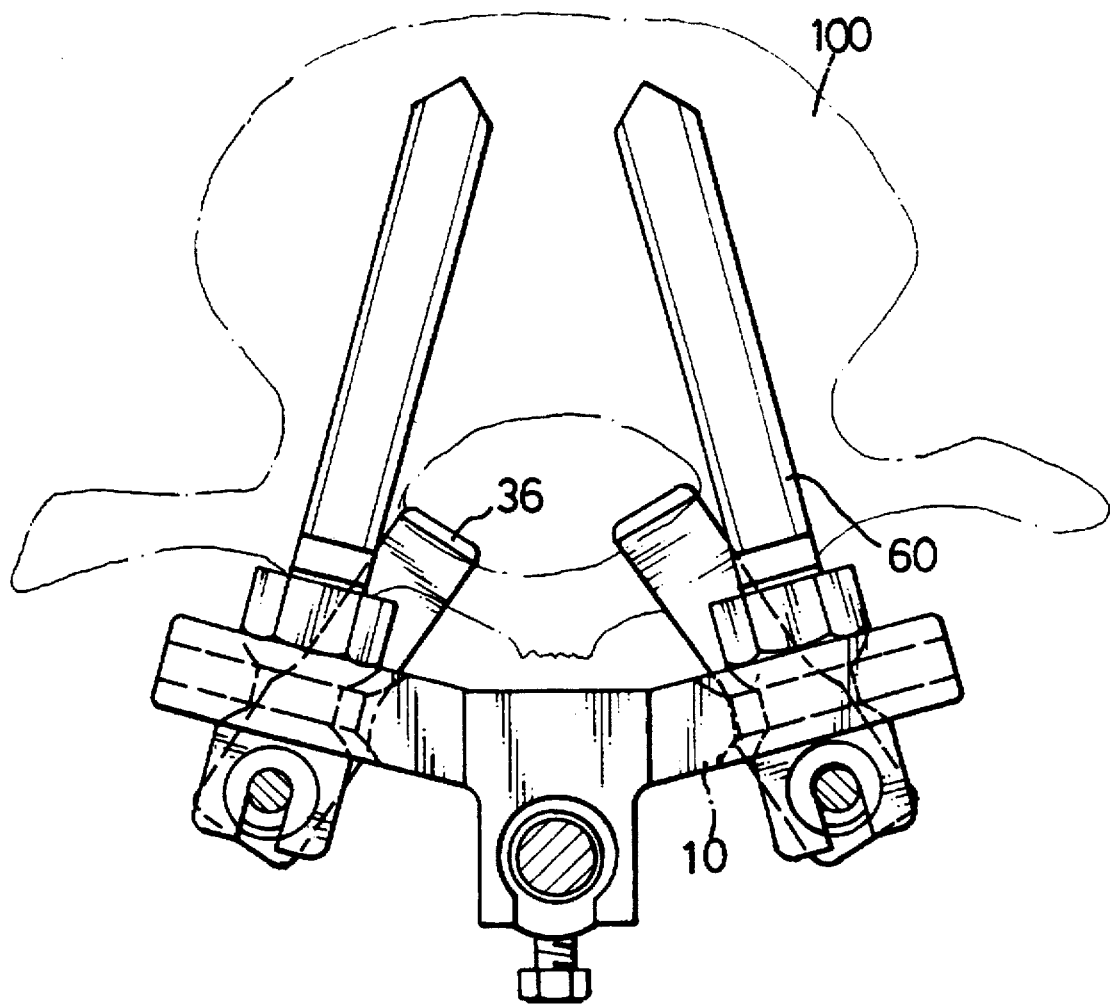
FIG. 7 is a schematic view of a coupling plate in combination with a laminal hook and a transpedicle screw.

Referring to FIG. 7, the coupling plate 10 is in cooperation with a transpedicle screw 60 and a laminal hook 36 to correct the deformed spine. Alternatively, the coupling plate 10 may cooperate with a transpedicle screw 60 and a pedicle hook. For the briefness of the specification, this modification is not shown.

Figure 8:
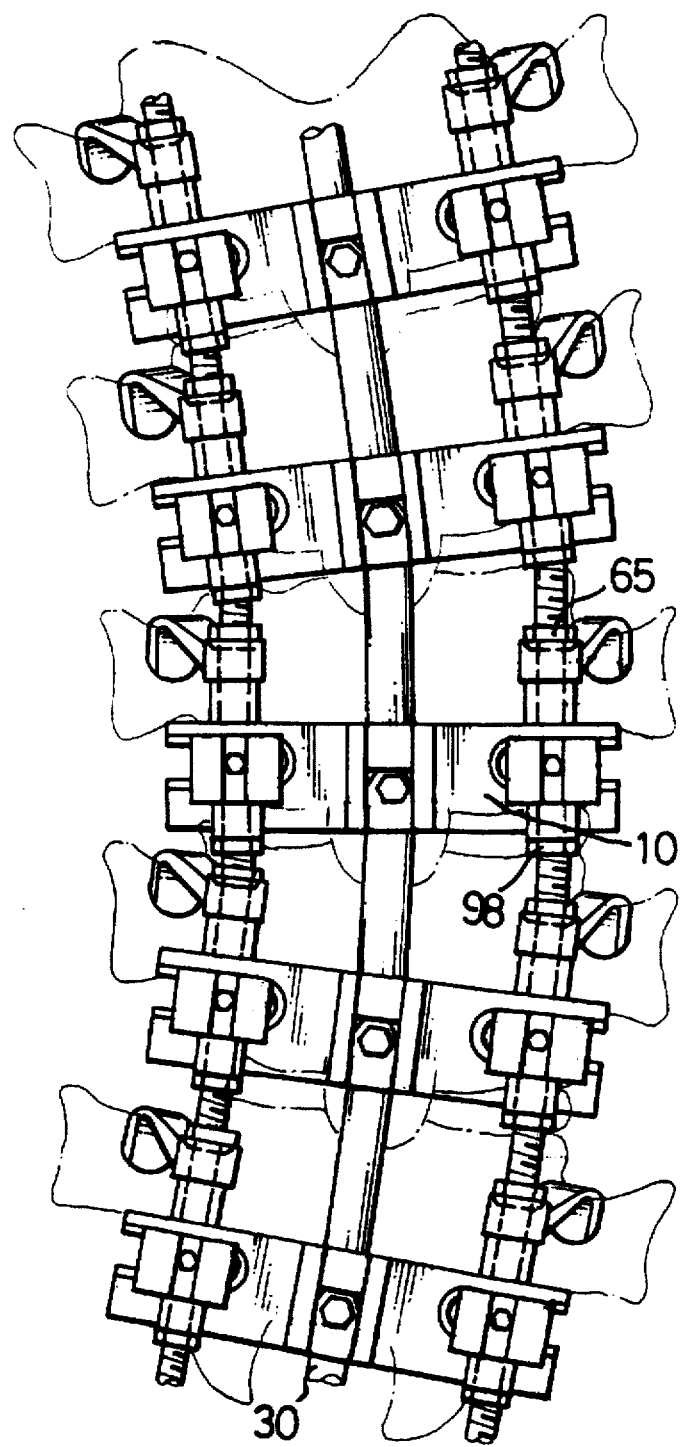
FIG. 8 is a schematic view of spine in combination with a plurality of coupling plates according to the present invention and the hook assemblies of FIG. 5.

A plurality of hook assemblies in combination with a corresponding number of coupling plates 10 is shown in FIG. 8. The spine can be corrected by turning the nuts 65 and 98 and adjusting the central rod 30.

Although the invention has been explained in relation to its preferred embodiment, it is to be understood that many other possible modifications and variations can be made without departing from the spirit and scope of the invention as hereinafter claimed.

What is claimed is:

1. An assembly for spinal correction comprising:

a central rod;

a clamping tube having a truncated conical head sized to receive the central rod, an integrally formed step, and a threaded inner periphery defining a hole for a screw to extend therethrough and clamp the central rod;

a plate having two slots each extending from a distal end toward a center portion of the plate with grooved edges on inner walls of the slots and a channel perpendicular to an interconnection axis of the slots with an opening for receiving the step of the clamping tube;

a plurality of transpedicle screw assemblies each comprising a transpedicle screw with a hole defining in a head of the screw, two recesses being radially oppositely formed on a shank of the screw adjacent to the head thereof for engaging with the slot of the plate and a threaded portion being formed next to the recesses, and a cap nut for engaging with the threaded portion of the screw and mounting the transpedicle screw onto the plate;

two threaded shafts, one extending through the hole in the head of one of the transpedicle screw assemblies on one side of the central rod and the other extending through the hole in the head of another of the transpedicle screw assemblies on the other side of the central rod; and a first nut and a second nut respectively threaded on each of the threaded shafts abutting the two ends of the hole in the head of each transpedicle screw so that a spinal correction is executed by turning the first and the second nuts.

2. An assembly for spinal correction as claimed in claim 1 further comprising a tubular piece and a pedicle hook being inserted between one of the first and the second nuts and the head of the transpedicle screw.

3. An assembly for spinal correction as claimed in claim 1 further comprising a tubular piece and a transverse process hook being provided between one of the first and the second nuts and the head of the transpedicle screw.

4. An assembly for spinal correction as claimed in claim 1 further comprising a tubular piece and a laminal hook being provided between one of the first and the second nuts and the head of the transpedicle screw.

* * * * *